United States Patent
Zhang et al.

(10) Patent No.: US 11,161,871 B2
(45) Date of Patent: Nov. 2, 2021

(54) CRYSTALLINE FORM OF OBETICHOLIC ACID AND PREPARATION METHOD THEREFOR

(71) Applicant: Jiangsu Hengrui Medicine Co., Ltd., Jiangsu (CN)

(72) Inventors: Shunji Zhang, Jiangsu (CN); Sheng Wang, Jiangsu (CN); Changzhen Zhu, Jiangsu (CN); Weiwei Tian, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 304 days.

(21) Appl. No.: 16/088,509

(22) PCT Filed: Mar. 30, 2017

(86) PCT No.: PCT/CN2017/078821
§ 371 (c)(1),
(2) Date: Sep. 26, 2018

(87) PCT Pub. No.: WO2017/167233
PCT Pub. Date: May 10, 2017

(65) Prior Publication Data
US 2020/0299324 A1    Sep. 24, 2020

(30) Foreign Application Priority Data

Mar. 31, 2016    (CN) .......................... 201610201130.0

(51) Int. Cl.
*C07J 9/00* (2006.01)
*A61P 1/16* (2006.01)

(52) U.S. Cl.
CPC .................. *C07J 9/005* (2013.01); *A61P 1/16* (2018.01); *C07B 2200/13* (2013.01)

(58) Field of Classification Search
CPC .............................. C07J 2200/13; C07J 9/005
See application file for complete search history.

(56) References Cited

FOREIGN PATENT DOCUMENTS

| CN | 201380043964.8 A | 7/2015 |
|---|---|---|
| CN | 105085597 A | 11/2015 |
| CN | 105175473 A | 12/2015 |
| CN | 105777836 A | 7/2016 |
| CN | 105810653 A | 7/2016 |
| CN | 105859814 A | 8/2016 |
| CN | 105985395 A | 10/2016 |
| WO | 2013192097 A1 | 12/2013 |
| WO | 2016045480 A1 | 3/2016 |
| WO | 2017008773 A1 | 1/2017 |

OTHER PUBLICATIONS

Bhattacharya et al. (Brittain, ed. Polymorphism in Pharmaceutical Solids, 2009, p. 334.*
Int'l Search Report dated Jun. 28, 2017 in Int'l Application No. PCT/CN2017/078821.

* cited by examiner

*Primary Examiner* — Susanna Moore
(74) *Attorney, Agent, or Firm* — Ice Miller LLP

(57) ABSTRACT

The present invention relates to a new crystalline form of obeticholic acid and a preparation method therefor. In particular, the present invention relates to crystal form E of obeticholic acid and a preparation method therefor. The crystalline form is very stable, and the solvent residue is low, and the crystalline form is suitable for industrial production. Obeticholic acid has the following structure:

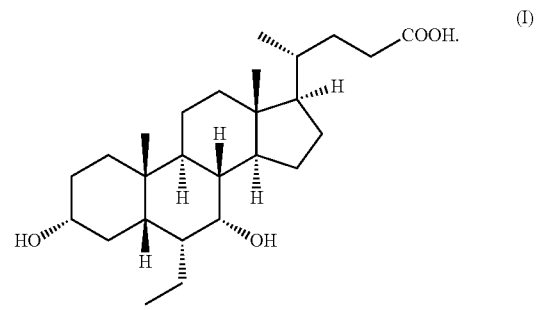

(I)

18 Claims, 2 Drawing Sheets

CRYSTALLINE FORM OF OBETICHOLIC ACID AND PREPARATION METHOD THEREFOR

CROSS-REFERENCE TO RELATED APPLICATION

This application is a Section 371 of International Application No. PCT/CN2017/078821, filed Mar. 30, 2017, which was published in the Chinese language on Oct. 5, 2017, under International Publication No. WO 2017/167233 A1, which claims priority under 35 U.S.C. § 119(b) to Chinese Application No. 201610201130.0, filed Mar. 31, 2016, the disclosures of which are incorporated herein by reference in their entirety.

FIELD OF THE INVENTION

The present invention relates to crystal form E of obeticholic acid and a preparation method thereof. The compound of formula (I) prepared according to the method of the present invention can be used in the treatment of primary biliary cirrhosis and nonalcoholic fatty liver disease.

BACKGROUND OF THE INVENTION

Obeticholic acid is a farnesoid X receptor agonist. It indirectly inhibits the gene expression of cytochrome 7A1 (CYP7A1) by activating the farnesoid X receptor. Since CYP7A1 is a rate-limiting enzyme of bile acid biosynthesis, obeticholic acid can inhibit the synthesis of bile acid, and can be used in the treatment of primary biliary cirrhosis and nonalcoholic fatty liver disease.

Obeticholic acid was successfully developed by Intercept Pharmaceuticals Inc. (USA), and is the first drug developed in the past 20 years for the treatment of cholestatic liver disease. It is useful for patients who cannot respond adequately to or tolerate the old standard treatment drug ursodeoxycholic acid. In a placebo-controlled phase III clinical trial, obeticholic acid (OCA) increases the level of two biomarkers associated with reduced risk of liver transplantation. The composite end point of clinical trial is that alkaline phosphatase is reduced by at least 15%, and the activity of serum alkaline phosphatase is 1.67 times lower than the normal upper limit, while bilirubin is in the normal range. Alkaline phosphatase is a biomarker used to indicate the severity of liver disease.

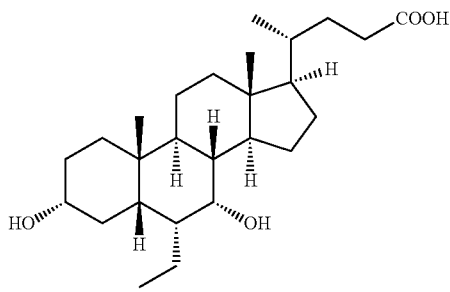

The patent application CN201380043964.8 of Intercept Pharmaceuticals Inc. (USA) discloses crystal form C of obeticholic acid. The preparation method is butyl acetate recrystallization method. The resulting crystal form C is a solvate. Due to the high boiling point of butyl acetate (126° C.), it is difficult to completely remove the solvent from the sample. In CN201380043964.8, drying under 80° C. is used in order to remove the solvent. However, obeticholic acid is highly unstable to heat, and drying under such a high temperature causes rapid degradation and generates new impurities. The degradation will be reduced if drying is carried out under a lower temperature, but that will make it difficult to remove the residual solvent. Therefore, there is still a need to find a crystallization method of obeticholic acid that avoids using a high boiling solvent.

SUMMARY OF THE INVENTION

The present invention provides obeticholic acid as shown in formula (I),

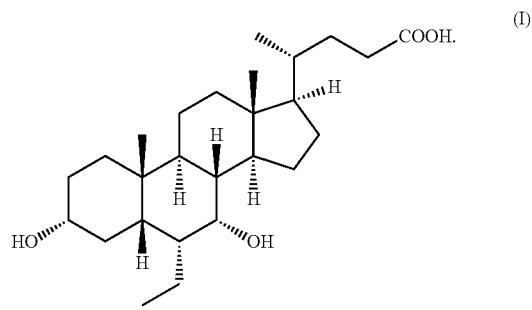

A crystal product of the compound of formula (I) can be obtained under a crystallization condition with an appropriate amount of solvent. X-ray diffraction and differential scanning calorimetry (DSC) measurements were conducted on the resulting crystal product. It was found that the crystal product is a crystal form with good stability, and is referred to as crystal form E. The DSC spectrum of crystal form E of the present application shows a melting endothermic peak at about 94.5° C. The X-ray powder diffraction spectrum, which is obtained by using Cu-Ka radiation and represented by 2θ angle, is shown in FIG. 1, in which there are characteristic peaks at about 3.07, 4.86, 5.21, 6.20, 7.15, 7.64, 8.18, 8.84, 9.86, 10.88, 12.31, 14.75, 15.28, 15.77, and 16.37. As is known in the art, the value of 2θ angle allows for a certain error, for example, 2θ±0.2 is considered to be within the same 2θ angle range.

The present invention also provides a method for preparing crystal form E of obeticholic acid, comprising the following steps of:

1) adding any crystal form or amorphous form of the compound of formula (I) into an appropriate amount of organic solvent, heating the solution until it is clear, and then cooling it to precipitate a crystal; and 2) filtering the crystal, then washing and drying it.

In step 1), the solvent is one or more selected from the group consisting of ethyl acetate, methyl acetate, propyl acetate, methyl formate, ethyl formate, and propyl formate, or the solvent is a mixed solvent of at least one of ethyl acetate, methyl acetate, propyl acetate, methyl formate, ethyl formate, and propyl formate with n-pentane, n-hexane, n-heptane or petroleum ether. Preferably, the solvent is a mixed solvent of n-hexane/ethyl acetate. In a preferred embodiment, the solvent is n-hexane/ethyl acetate. The resulting crystal form of the compound of formula (I) is determined by differential scanning calorimetry (DSC) and X-ray diffraction spectrum. Meanwhile, the residual solvent in the resulting crystal is also determined.

Crystal form E of the compound of formula (I) prepared according to the method of the present invention does not contain or contains only a relatively low content of residual solvent, which meets the requirement of the National Pharmacopoeia concerning the limitation of the residual solvent of pharmaceutical products. Therefore, the crystal of the present invention is suitable for use as a pharmaceutical active ingredient.

Since n-hexane, ethyl acetate, etc. are low boiling solvents which are readily removed during the drying process, the crystal form E of obeticholic acid prepared according to the method of the present application can reach constant weight merely by blast drying at 30° C. for 1-2 hours. However, the crystal form C of obeticholic acid prepared according to the butyl acetate crystallization method disclosed in patent application CN201380043964.8 reaches constant weight by blast drying at 50° C. for 4 hours, and there is still a considerable residual amount of butyl acetate.

The research results show that crystal form E of the compound of formula (I) prepared according to present invention is stable under conditions of lighting, high temperature and high humidity. Crystal form E is also stable under conditions of grinding, pressure and heating, which meets the production, transportation and storage requirements of drug products. The preparation process thereof is stable and controllable, which is suitable for industrial production.

The applicant dried the crystal product at 80° C. crystallized with butyl acetate according to CN201380043964.8, and found that the color of the resulting solid changed, indicating that obeticholic acid is unstable at 80° C. and has undergone degradation. When the crystal form C was dried at 50-60° C., it was determined that the residual amount of butyl acetate is about 6800 ppm. After transforming this crystal form to an amorphous sample, the residual amount of butyl acetate is still up to about 1800 ppm. However, after transforming the crystal form E obtained by the method of the present invention to an amorphous sample, the residual amount of solvent is very low. The results of three batches of tests are as follows: in the first batch, no solvent is detected; in the second batch, ethyl acetate is 150 ppm and tetrahydrofuran is 10 ppm; and in the third batch, ethyl acetate is 35 ppm and tetrahydrofuran is 10 ppm.

In another aspect, the present invention provides a method for purifying obeticholic acid, comprising a step of transforming crude obeticholic acid to the crystal form E. Preferably, the transformation comprises a step of recrystallizing obeticholic acid with a solvent, wherein the solvent is one or more selected from the group consisting of ethyl acetate, methyl acetate, propyl acetate, methyl formate, ethyl formate, and propyl formate, or the solvent is a mixed solvent of at least one of ethyl acetate, methyl acetate, propyl acetate, methyl formate, ethyl formate, and propyl formate with n-pentane, n-hexane, n-heptane or petroleum ether. Preferably, the solvent is a mixed solvent of n-hexane/ethyl acetate. The crude obeticholic acid used in the purification method can be prepared by any method, and the purity of which is not limited. In particular, according to the present invention, the purity of obeticholic acid can be further improved by the step of transforming crude obeticholic acid with a high purity, for example, crude obeticholic acid with a purity higher than 98% or 99%, to the crystal form E.

More preferably, the purification method also comprises a step of transforming the crystal form E of obeticholic acid to an amorphous form. The transformation method is well known in the art, for example, the step of transforming the crystal form E to an amorphous form can comprise a step of dissolving the crystal form E of obeticholic acid in a base, and then precipitating it with an acid. Preferably, the base is an inorganic base, and more preferably an aqueous NaOH solution. Preferably, the acid is an inorganic acid, and more preferably hydrochloric acid.

Although crude obeticholic acid prepared by conventional methods has high purity, but still contains a relatively high content of impurities, which is a safety hazard for pharmaceutical use. The purification method of the present invention makes it possible to further improve the purity of crude obeticholic acid which has already had a high purity, and enables the content of total impurities determined by HPLC to not exceed 0.5%, preferably not exceed 0.4%, and more preferably not exceed 0.3%.

DETAILED DESCRIPTION OF THE INVENTION

The present invention will be illustrated by the following examples in detail. The examples of the present invention are merely intended to describe the technical solution of the present invention, and should not be considered as limiting the scope of the present invention.

Test instruments used in the experiments

1. DSC Spectrum
Instrument type: MettlerToledo DSC 1 Staree System
Purging gas: Nitrogen
Heating rate: 10.0° C./min
Temperature range: 40-350° C.
2. X-Ray Diffraction Spectrum
Instrument type: Bruker D8 Focus X-ray powder diffractometer
Ray: monochromatic Cu-Kα ray (λ=1.5406)
Scanning mode: θ/2θ, Scanning range: 2-40°
Voltage: 40 KV, Electric current: 40 mA

EXAMPLE 1

Figure 1:
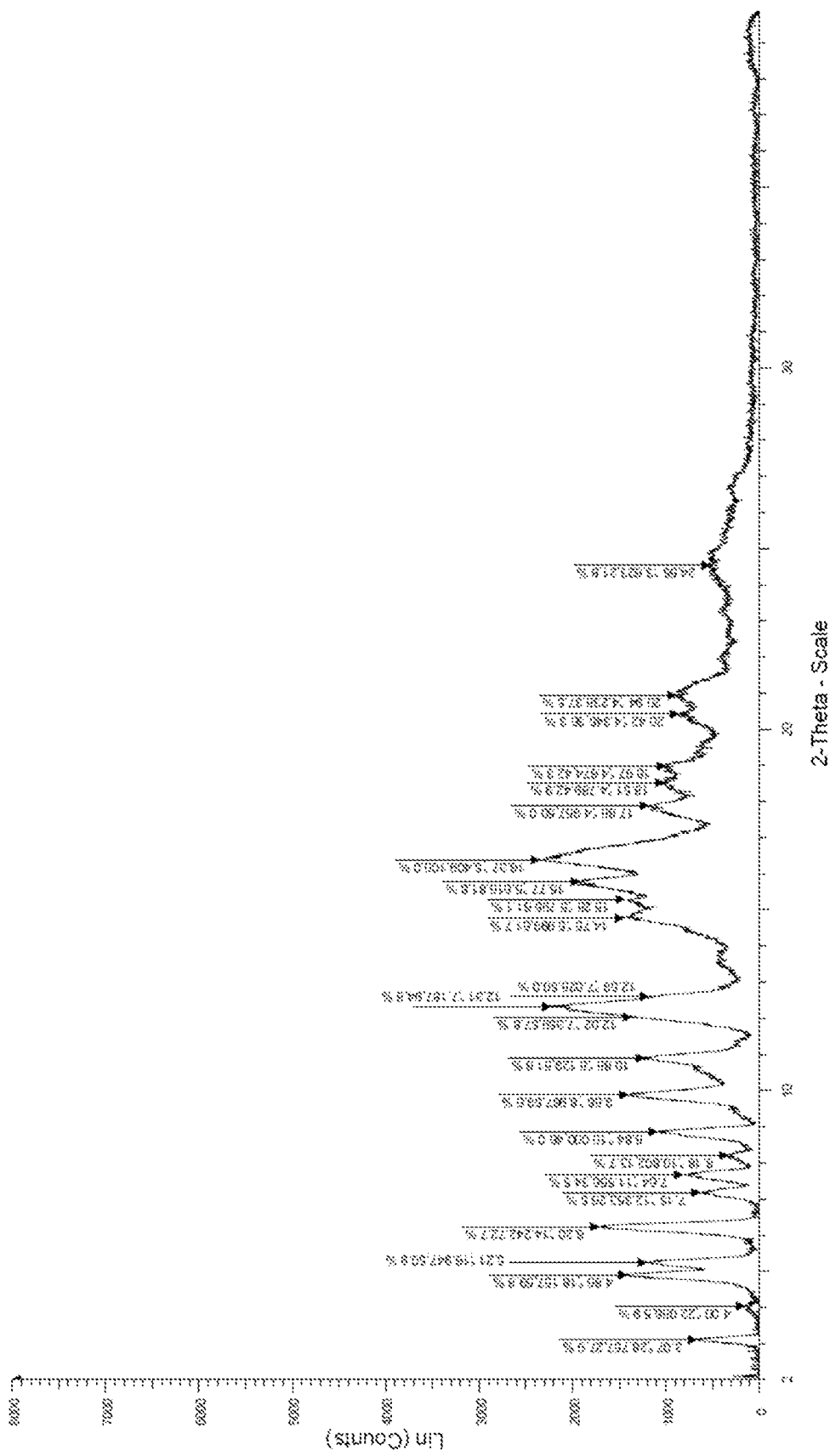
FIG. 1 shows the X-ray powder diffraction spectrum of crystal form E of the compound of formula (I).
Figure 2:
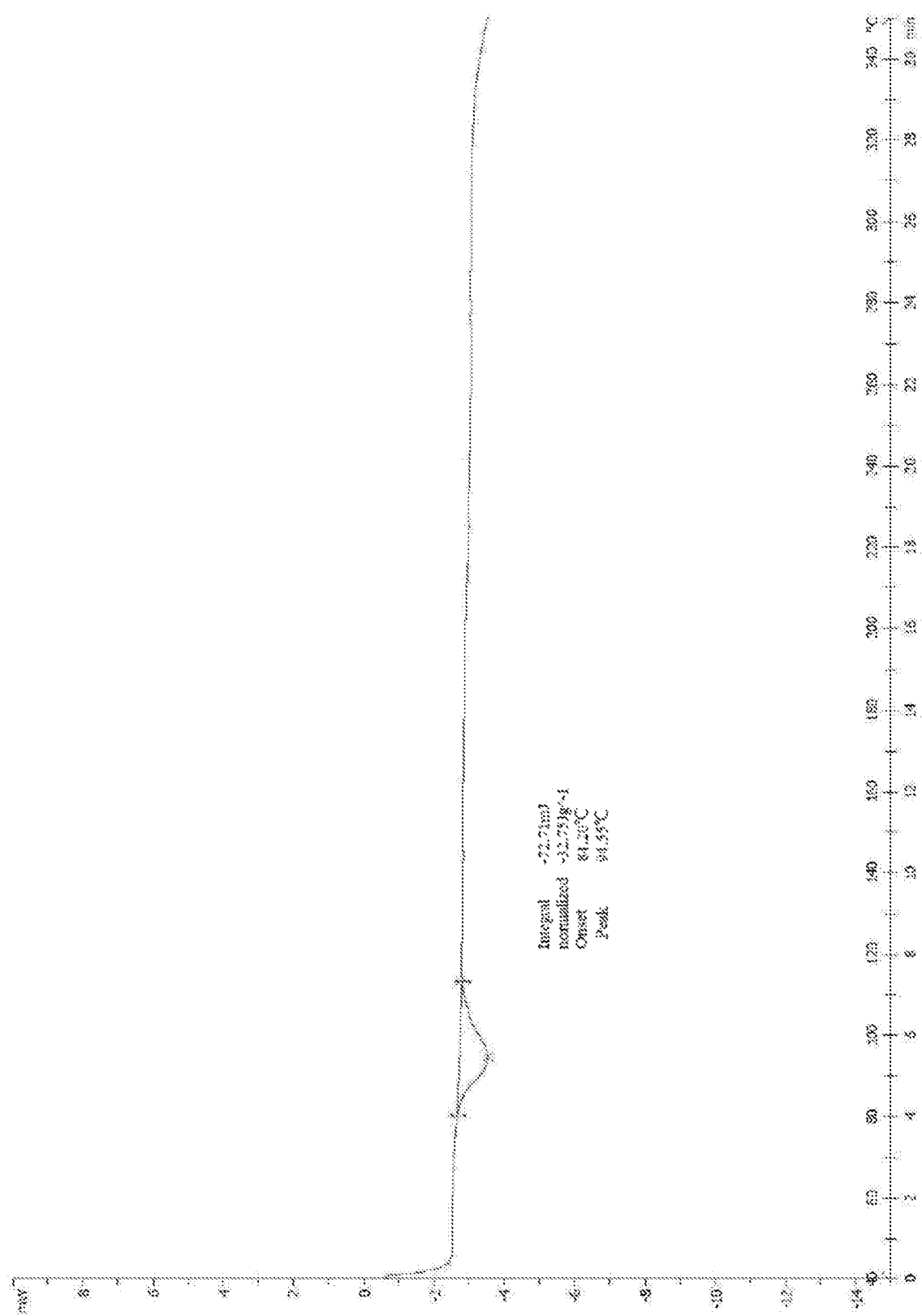
FIG. 2 shows the DSC spectrum of crystal form E of the compound of formula (I).

1.0 g of the compound of formula (I) (crystal form C, prepared by the method disclosed in CN201380043964.8) was added to a 10 ml conical flask, followed by addition of 2 ml of n-hexane and 2 ml of ethyl acetate. The mixture was heated to 60° C. to make the solution clear, and then naturally cooled to room temperature and stirred for 20 hours. The mixture was filtered, and then blast dried at 30° C. for 2 hours to obtain a solid (0.8 g, yield: 80%). The X-ray powder diffraction spectrum of the crystal sample is shown in FIG. 1. There are characteristic peaks at about 3.07, 4.86, 5.21, 6.20, 7.15, 7.64, 8.18, 8.84, 9.86, 10.88, 12.31, 14.75, 15.28, 15.77, and 16.37. The DSC spectrum is shown in FIG. 2, having a sharp melting endothermic peak at 94.5° C. The crystal form was defined as crystal form E.

EXAMPLE 2

1.0 g of the compound of formula (I) (amorphous form) was added to a 10 ml conical flask, followed by addition of 2 ml of ethyl acetate. The mixture was heated to 65° C. to make the solution clear, and then naturally cooled to room temperature and stirred for 20 hours. The mixture was filtered, and then blast dried at 40° C. for 1 hour to obtain a solid (0.5 g, yield: 50%). The product was identified as crystal form E after studying and comparing the X-ray diffraction and DSC spectra.

EXAMPLE 3

1.0 g of the compound of formula (I) (amorphous form) was added to a 10 ml conical flask, followed by addition of 3 ml of ethyl formate. The mixture was heated to 50° C. to make the solution clear, and then naturally cooled to room temperature and stirred for 20 hours. The mixture was filtered, and then dried in a vacuum at 30° C. for 4 hours to obtain a solid (0.6 g, yield: 60%). The product was identified as crystal form E after studying and comparing the X-ray diffraction and DSC spectra.

EXAMPLE 4

1.0 g of the compound of formula (I) (amorphous form) was added to a 10 ml conical flask, followed by addition of 2 ml of ethyl acetate and 3 ml of n-heptane. The mixture was heated to 60° C. to make the solution clear, and then naturally cooled to room temperature and stirred for 20 hours. The mixture was filtered, and then dried in a vacuum at 30° C. for 4 hours to obtain a solid (0.85 g, yield: 85%). The product was identified as crystal form E after studying and comparing the X-ray diffraction and DSC spectra.

EXAMPLE 5

The sample of crystal form E prepared in Example 1 was spread flat in the air to test its stability under conditions of lighting (4500 Lux), heating (40° C., 60° C.), and high humidity (RH 75%, RH 90%), respectively. Samplings were carried out on Day 5 and Day 10. The purity as detected by HPLC is shown in Table 1.

TABLE 1

Stability comparison of the sample of crystal form E of the compound of formula (I)

| Batch number | Time (day) | Lighting | 40° C. | 60° C. | RH 75% | RH 90% |
|---|---|---|---|---|---|---|
| Crystal form E | 0 | 99.7% | 99.7% | 99.7% | 99.7% | 99.7% |
|  | 5 | 99.6% | 99.6% | 99.4% | 99.7% | 99.6% |
|  | 10 | 99.6% | 99.5% | 99.1% | 99.7% | 99.5% |

The results of the stability study showed that the sample of crystal form E of the compound of formula (I) had good stability when it was spread flat in the air under conditions of lighting/high humidity, while the sample was slightly degraded under a condition of high temperature.

EXAMPLE 6

Crystal form E of the compound of formula (I) prepared according to the method of Example 1 was ground, heated or tableted. The results showed that the crystal form was stable. The detailed experimental data are shown in Table 2 below.

TABLE 2

Special stability study of crystal form E of the compound of formula (I)

| Batch number | Treatment Process | Experimental procedure | Crystal form | DSC peak |
|---|---|---|---|---|
| Crystal form E | Grinding treatment for 10 minutes | 1 g of the sample of crystal form E of the compound of formula (I) was ground for 10 minutes in a mortar under nitrogen atmosphere. | Crystal form E | 94.3° C. |
|  | Heating treatment for 3 hours at 80° C. | 1 g of the sample of crystal form E of the compound of formula (I) was spread flat and heated at 80° C. for 3 hours. | Crystal form E | 94.5° C. |
|  | Tableting treatment | The sample of crystal form E of the compound of formula (I) was tableted. | Crystal form E | 94.6° C. |

EXAMPLE 7

The stability of crystal form E of the compound of formula (I) prepared according to the method of Example 1 was tested under a placement condition (30° C., RH 65%). Samplings were carried out on Day 5, Day 10, and Day 30. The results showed that the crystal form E was stable under the placement condition. The experimental data are shown in Table 3.

TABLE 3

Stability study of crystal form E of the compound of formula (I)

| Batch number | Time | Purity determined by HPLC | Crystal form (X-ray powder diffraction) |
|---|---|---|---|
| Crystal form E S051407170104 | Day 0 | 99.75% | Crystal form E |
|  | Day 5 | 99.72% | Crystal form E |
|  | Day 10 | 99.73% | Crystal form E |
|  | Day 30 | 99.70% | Crystal form E |

EXAMPLE 8

80 ml of tetrahydrofuran, 8 ml of hydrochloric acid, and 15 ml of purified water were added to 5.0 g of 6α-ethyl-3α-(methoxymethoxy)-7α-hydroxy-5β-cholane-24-acid (which can be prepared according to the method disclosed in WO2016045480), and the reaction was carried out at room temperature for 12 hours. The reaction solution was concentrated under reduced pressure, 30 ml of ethyl acetate and 10 ml of purified water were added to the residue, and then two phases were separated. The organic phase was washed with water, dried over anhydrous sodium sulfate, filtered and concentrated under reduced pressure. Then, 10 ml of n-hexane and 5 ml of ethyl acetate were added to the residue, and the mixture was heated to 60° C. and stirred for 30 minutes, and then cooled to precipitate a crystal. The mixture was filtered to obtain 3.1 g of crude obeticholic acid (the purity is 99.29% determined by HPLC, wherein the content of impurity A is 0.42%). Then, 6 ml of n-hexane and 6 ml of ethyl acetate were added to the crude product, and the mixture was heated to 60° C. to make the solution clear, and then naturally cooled to room temperature and stirred for 20 hours. The mixture was filtered, and then blast dried at 50° C. for 2 hours to obtain 2.1 g of crystal form E solid (the purity is 99.75% determined by HPLC, wherein the content of impurity A is 0.21%).

2.1 g of crystal form E solid was dissolved in a sodium hydroxide solution (prepared by dissolving 0.6 g of sodium hydroxide in 15 ml of purified water). The resulting solution was added dropwise to a hydrochloric acid solution (prepared by dissolving 0.15 ml of hydrochloric acid in 15 ml of purified water), and the mixture was stirred for 1 hour and filtered. The filter cake was washed for 4 times and dried under reduced pressure to obtain 1.7 g of amorphous solid (the purity is 99.70% determined by HPLC, wherein the content of impurity A is 0.22%).

The result showed that the recrystallization with n-hexane/ethyl acetate can effectively improve the purity of the sample. There is no significant change in purity when the crystal form E is transformed to an amorphous form.

What is claimed is:

1. Crystal form E of a compound of formula (I), wherein an X-ray powder diffraction spectrum of crystal form E comprises characteristic peaks at diffraction angles 0.2 of about 3.07, 4.86, 5.21, 6.20, 7.15, 7.64, 8.18, 8.84, 9.86, 10.88, 12.31, 14.75, 15.28, 15.77, and 16.37,

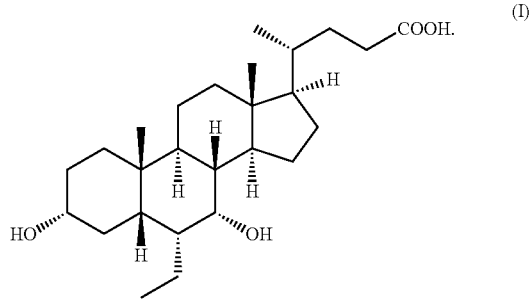

2. A method of preparing the crystal form E of the compound of formula (I) according to claim 1, comprising:
 1) adding a crystal form or amorphous form of the compound of formula (I) into an appropriate amount of solvent to obtain a mixture, heating the mixture to obtain a solution, and then cooling the solution to precipitate a crystal, wherein the solvent is one or more selected from the group consisting of ethyl acetate, methyl acetate, propyl acetate, methyl formate, ethyl formate, and propyl formate, or the solvent is a mixed solvent of one or more selected from the group consisting of ethyl acetate, methyl acetate, propyl acetate, methyl formate, ethyl formate, and propyl formate with n-pentane, n-hexane, n-heptane or petroleum ether; and
 2) filtering the crystal and drying the crystal.

3. A pharmaceutical composition, comprising the crystal form E according to claim 1, and a pharmaceutically acceptable carrier.

4. A method for purifying obeticholic acid, comprising transforming crude obeticholic acid to the crystal form E according to claim 1.

5. The method according to claim 4, wherein the transforming crude obeticholic acid to the crystal form E comprises recrystallizing the crude obeticholic acid with a solvent, wherein the solvent is one or more selected from the group consisting of ethyl acetate, methyl acetate, propyl acetate, methyl formate, ethyl formate, and propyl formate, or the solvent is a mixed solvent of one or more selected from the group consisting of ethyl acetate, methyl acetate, propyl acetate, methyl formate, ethyl formate, and propyl formate with n-pentane, n-hexane, n-heptane or petroleum ether.

6. The method according to claim 4, further comprising separating the crystal form E.

7. The method according to claim 6, further comprising transforming the crystal form E to an amorphous form or other crystal form.

8. The method according to claim 7, wherein the transforming the crystal form E to an amorphous form comprises dissolving the crystal form E in a base to obtain a solution, and precipitating the solution with an acid.

9. The method according to claim 8, wherein the base is an inorganic base.

10. The method according to claim 8, wherein the acid is an inorganic acid.

11. Crystal form E of a compound of formula (I):

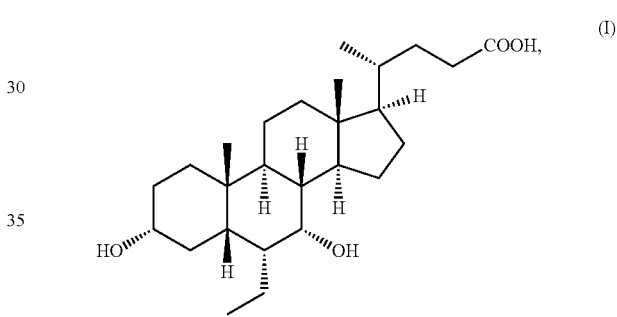

wherein the crystal form E has a characteristic X-ray powder diffraction spectrum as shown in FIG. 1.

12. The crystal form E according to claim 1, wherein a characteristic differential scanning calorimetry (DSC) spectrum comprises an endothermic peak at 94.5° C.

13. The method according to claim 2, wherein the mixed solvent is n-hexane/ethyl acetate.

14. A method of treating primary biliary cirrhosis or nonalcoholic fatty liver disease, comprising administering to a subject the pharmaceutical composition according to claim 3.

15. The method according to claim 5, wherein the mixed solvent is n-hexane/ethyl acetate.

16. The method according to claim 9, wherein the crystal form E is separated by filtration.

17. The method according to claim 10, wherein the base is an aqueous NaOH solution.

18. The method according to claim 10, wherein the acid is hydrochloric acid.

* * * * *